United States Patent [19]

Bailey

[11] 4,446,715

[45] May 8, 1984

[54] TRANSDUCER CALIBRATION SYSTEM

[75] Inventor: Wilber H. Bailey, Leucadia, Calif.

[73] Assignee: Camino Laboratories, Inc., San Diego, Calif.

[21] Appl. No.: 385,492

[22] Filed: Jun. 7, 1982

[51] Int. Cl.³ .................... G01K 15/00; G01L 27/00
[52] U.S. Cl. .................................. 73/1 R; 364/571
[58] Field of Search ............. 73/1 R, 4 R, 4 U, 4 D, 73/432 A; 364/571, 573; 324/130; 374/1, 2

[56] References Cited

U.S. PATENT DOCUMENTS

| | | | |
|---|---|---|---|
| 2,951,200 | 8/1960 | Critchlow | 364/571 X |
| 3,439,258 | 4/1969 | Van Leeuwen | 323/367 |
| 3,531,978 | 10/1970 | Yeager | 73/4 V |
| 3,535,637 | 10/1970 | Goransson | 324/130 |
| 3,740,533 | 6/1973 | Van Zeggeler | 73/1 R X |
| 3,757,217 | 9/1973 | Pearson | 324/151 R |
| 3,905,229 | 9/1975 | Togo et al. | 364/571 X |
| 3,976,150 | 8/1976 | Wilson et al. | 73/432 A X |
| 4,000,643 | 1/1977 | Pearson | 364/571 X |
| 4,038,532 | 7/1977 | Burris et al. | 364/571 X |
| 4,064,396 | 12/1977 | Panarello | 364/573 |
| 4,082,998 | 4/1978 | Marriott | 324/130 X |
| 4,179,745 | 12/1979 | Wuertele | 364/571 |
| 4,192,005 | 3/1980 | Kurtz | 364/571 |
| 4,218,916 | 8/1980 | Mutziger | 73/432 A X |
| 4,263,803 | 4/1981 | Burkhardt | 73/1 R |
| 4,282,578 | 8/1981 | Payne et al. | 364/573 |
| 4,290,297 | 9/1981 | Anderson | 73/1 R |
| 4,323,972 | 4/1982 | Winter | 365/571 X |
| 4,331,026 | 5/1982 | Howard et al. | 73/1 R X |
| 4,337,638 | 7/1982 | Leonard et al. | 73/1 R |
| 4,349,886 | 9/1982 | Ibar | 364/571 X |

OTHER PUBLICATIONS

"Nth Order Regression," *Science and Engineering Programs Apple II Edition*, 1981.

Primary Examiner—Gerald Goldberg
Assistant Examiner—Tom Noland
Attorney, Agent, or Firm—Fulwider, Patton, Rieber, Lee & Utecht

[57] ABSTRACT

A transducer system that provides accurate measurements of a physical variable such as pressure for any one of a number of different transducers. Each transducer includes special calibration indicators for identifying any inaccuracies in its output signal, and monitoring and correcting circuitry is selectively attachable to any one of the transducers, to read the calibration indicators and apropriately adjust the transducer's output signal, thereby correcting for the identified inaccuracies.

17 Claims, 4 Drawing Figures

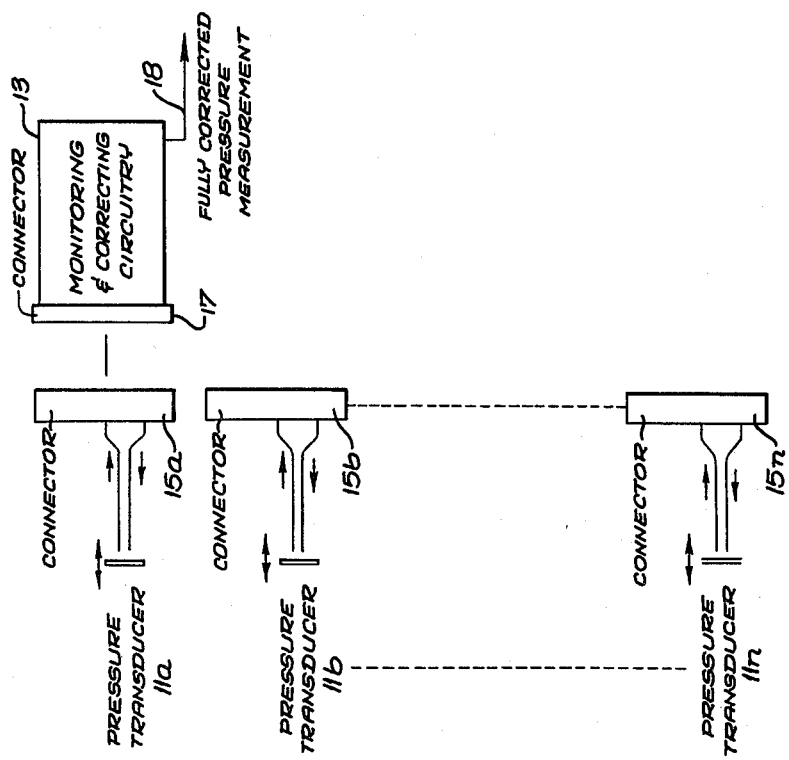

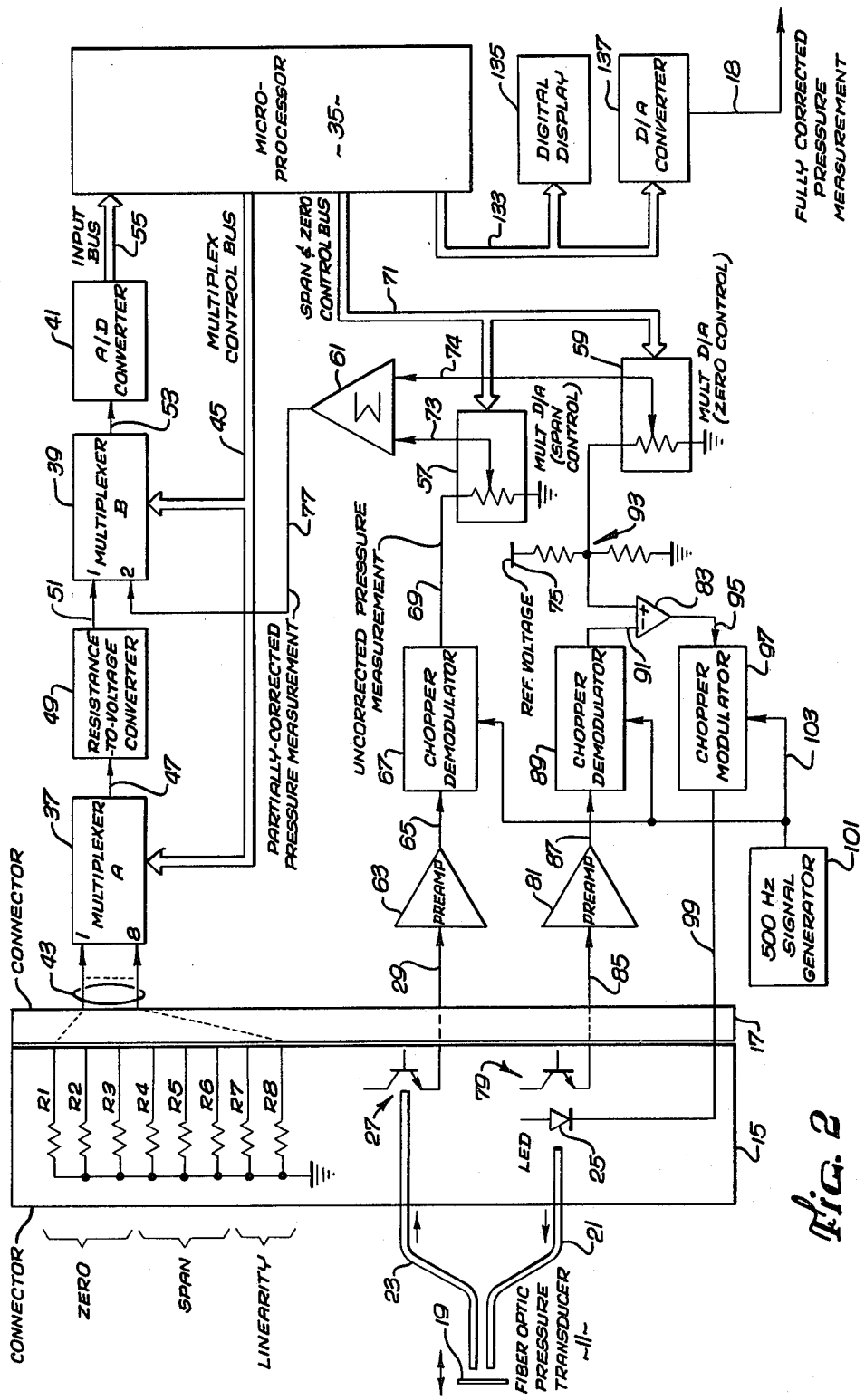

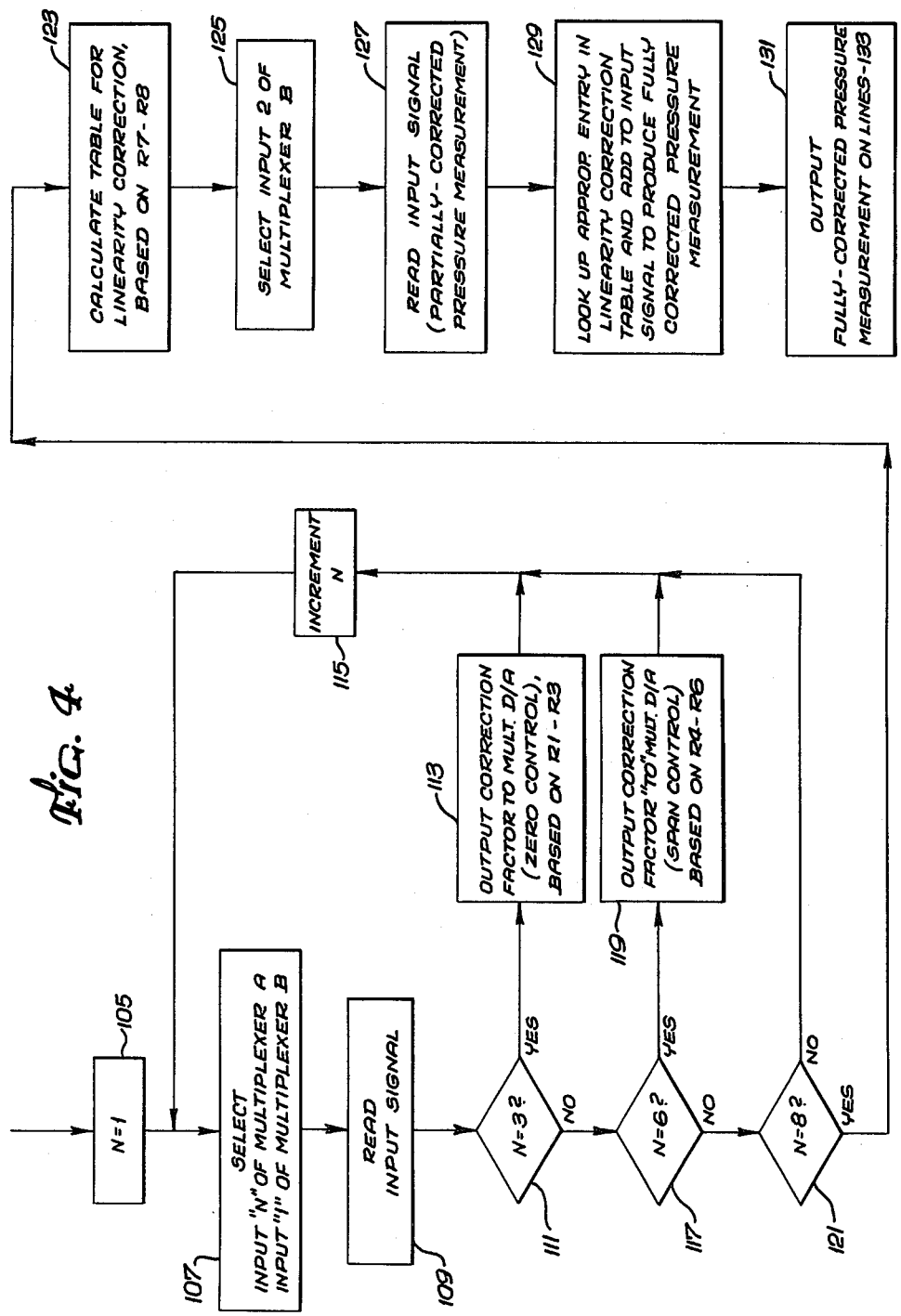

TRANSDUCER CALIBRATION SYSTEM

BACKGROUND OF THE INVENTION

This invention relates generally to transducer systems for measuring prescribed physical variables, and more particularly to transducer systems having special calibration means for use in correcting any inaccuracies in the transducers' output signals.

In the past, transducers of accuracy and high precision were ordinarily produced by manufacturing them with extreme care, at relatively great expense. Some transducer systems included trimming means for adjusting the transducer's output signal such that the system provides closer to a desired transfer characteristic. However, this technique can likewise be expensive if higher order corrections must be made to the signal.

The transducer systems described above are not believed to be completely satisfactory in many situations, such as in hospital environments where numerous different pressure transducers and temperature transducers (i.e., thermometers) are used every day. This is because there is a strong need for accuracy and precision, yet there is also a need for minimizing expense. It therefore should be appreciated that there is a need for a transducer system that can be utilized with relatively inexpensive or disposable transducers, yet can provide high accuracy and precision. The present invention fulfills this need.

SUMMARY OF THE INVENTION

The present invention is embodied in a transducer system for measuring a prescribed physical variable. The system includes transducer means for monitoring the physical variable and producing a signal indicative of it, the signal differing from a desired relationship with the physical variable in a predetermined fashion. In accordance with the invention, the system further includes calibration means for characterizing the difference between the signal and its desired relationship with the variable, and correcting means responsive to the calibration means for adjusting the signal in a prescribed fashion, to produce a corrected measure of the physical variable.

More particularly, the transducer system is of particular value if it includes a plurality of separate transducer means, each associated with a separate calibration means. A single correcting means is selectively connected to each transducer means, to adjust its output signal in accordance with the associated calibration means, to produce a corrected measure of the physical variable being monitored. In this manner, each transducer means can be made relatively inexpensively, yet with the correcting means, can provide an output signal of high accuracy and precision. The transducer and correcting means are carried on, i.e. connected with, a connection element designed for connection to processing circuitry. Obviously the carrier can be made compact and insertable into a body for biological measurements.

In the preferred embodiment, the calibration means includes a plurality of indicia, such as a plurality of resistors of selected resistance, for characterizing the transducer means' inaccuracy. In particular, first, second, and third sets of the plurality of resistors characterize the zero level error, the span error, and linearity error, respectively, of the difference between the transducer means signal and its desired relationship with the physical variable. The correcting means measures the resistance of each resistor in a sequential fashion, and then adjusts the transducer means signal by adding to it a first correction factor to correct its zero level, multiplying it by a second correction factor to correct its span, and adding to it a third correction factor to correct its linearity.

Other aspects and advantages of the present invention should become apparent from the following description of the preferred embodiment, taken in conjunction with the accompanying drawings, which illustrate, by way of example, the principles of the invention.

BRIEF DESCRIPTION OF THE DRAWINGS

FIG. 1 is a simplified block diagram of a pressure transducer system for producing a corrected pressure measurement for a selected one of a plurality of optical pressure transducers;

FIG. 3 is a graph of the transducing characteristic of a typical one of the pressure transducer of FIG. 1, depicting its zero level error, span error, and linearity error, which are corrected by the monitoring and correcting circuitry of FIG. 1; and FIG. 4 is a simplified flowchart of the operational steps followed by the microprocessor depicted in FIG. 2.

DESCRIPTION OF THE PREFERRED EMBODIMENT

Figure 2:
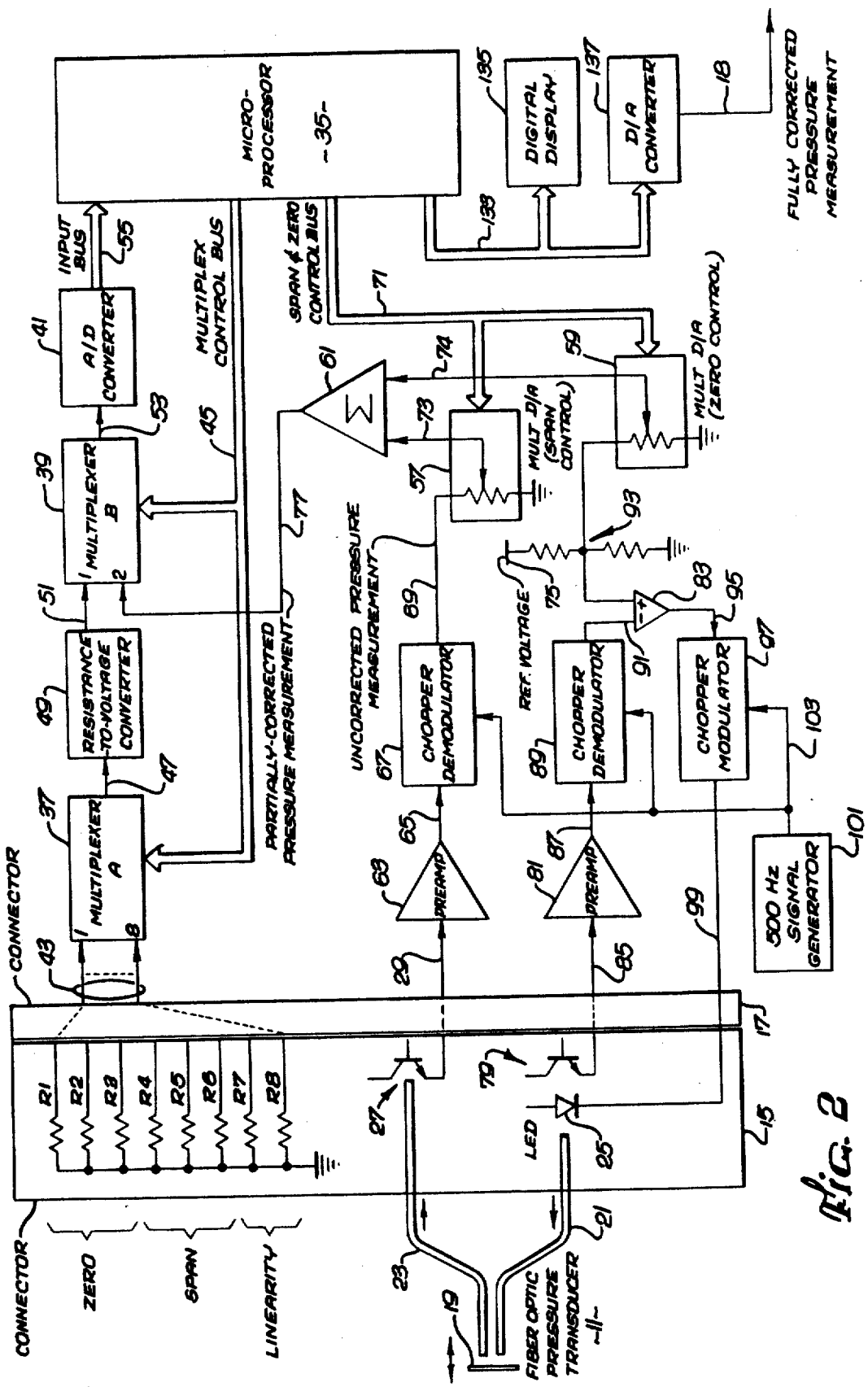
FIG. 2 is a block diagram of the monitoring and correcting circuitry of FIG. 1, shown connected to a selected one of the pressure transducers.

Referring now to the drawings, and particularly to FIG. 1, there is shown a pressure transducer system for providing an accurate pressure measurement for any of a plurality of separate locations. The system includes a plurality of pressure transducers, designated 11a-11n, and monitoring and correcting circuitry 13 for selectively monitoring and correcting the pressure signal produced by any one of the transducers. Each transducer includes its own electrical connector, designated 15a-15n, and the monitoring and correcting circuitry includes a single connector 17, which is selectively attachable to any one of the transducer connectors.

In accordance with the invention, each of the transducer connectors 15a-15n carries indicators characterizing the accuracy of the corresponding transducer's output signal, and the monitoring and correcting circuitry 13 is responsive to the indicators to adjust the signal appropriately. In particular, the indicators indicate the errors in zero level, span and linearity of the signal actually output by the transducer 11, as compared to its desired relationship with the pressure being measured. The signal's zero level and span are corrected while it is in its original analog format, whereas its linearity is corrected after it has been converted to a corresponding digital format. The circuitry outputs a corrected pressure measurement signal on line 18, which more accurately represents the pressure being measured.

Since the transducer output signal is to be corrected, the transducer 11 needn't be highly accurate and can be manufactured with substantially less precision. This of course reduces costs substantially.

Referring now to FIG. 2, there is depicted a simplified block diagram of the monitoring and correcting circuitry 13 of FIG. 1, shown connected to a particular one of the plurality of pressure transducers 11a–11n. The transducer is depicted to include a movable diaphragm 19, first and second optical fibers 21 and 23, an LED light source 25 and a phototransistor 27. Light from the LED is transmitted down the first optical fiber to impinge on the diaphragm, which reflects it back along the second optical fiber to impinge on the phototransistor. The movable diaphragm's position varies in accordance with the pressure to be measured, and the amount of light it reflects back along the second optical fiber varies in accordance with that position. The electrical current output by the phototransistor on line 29 therefore varies in accordance with the pressure being monitored.

The indicators carried by the transducer connector 15 comprise eight resistors, designated R1–R8, for characterizing the accuracy of the transducer's uncorrected output signal present on line 29. The particular resistances of the resistors are specially selected during manufacture of the transducer 11, to identify the particular corrections that must be made by the monitoring and correcting circuitry 13 in order to make the transducer's output signal a more accurate indication of the actual pressure being measured.

In the graph of FIG. 3, a solid line 31 depicts the amplitude of the signal output by a typical pressure transducer 11 for a range of actual pressures, as determined during manufacture of the transducer. This actual transducing characteristic can be compared to the transducer's desired transducing characteristic, which is depicted by the dotted line 33 and which represents the signal output by a perfect transducer. The difference between the actual curve 31 and the desired curve 33 represents the transducer's inaccuracy of error.

The resistors R1–R8 contained in the transducer connector 15 identify certain characteristics of the transducer's inaccuracy, so that the monitoring and correcting circuitry 13 can adjust the transducer's output signal appropriately. In particular resistors R1–R3 identify the offset in the transducer's output signal at zero pressure, resistors R4–R6 identify the difference between the span of the transducer's actual output signal and the span of its desired output signal, and resistors R7–R8 identify the degree of non-linearity in the transducer's output signal.

The specific resistance value for each of the resistors R1–R8 is selected during manufacture of the transducer 11. These values reflect the coefficients of a general curve fit equation, and are derived using a suitable computer program, such as provided in an article entitled "Nth Order Regression," *Science and Engineering Programs Apple II Edition*, published by McGraw Hill, 1981. When correcting for zero level, span and linearity (i.e., zero, first and second order correction), the curve fit equation is:

$$P = A_0 + A_1 x + A_2 x^2$$

where
P = actual pressure,
$A_0$ = zero level correction,
$A_1$ = span correction,
$A_2$ = linearity correction,
x = transducer output.

Higher order corrections could of course be made for more complex curves, using additional resistors to reflect the higher order coefficients.

The resistors R1–R8 are each selected from a set in which the successive resistances vary linearly, i.e., with equal differences between the successive values, or geometrically, i.e., with progressive increases between the successive values. In the latter case, the set of possible resistances can conveniently include alternate values from a standard 1% or 5% series. If the set of possible resistances includes 16 values, each resistor can represent four bits of binary data. The magnitude and direction of the transducer's zero level error and span error could therefore both be characterized by 12 bits of data, and the magnitude and direction of its linearity error could be characterized by 8 bits of data.

Referring again to FIG. 2, the monitoring and correcting circuitry 13 first reads each of the eight resistors R1–R8 in succession, and then reads the uncorrected transducer output signal and adjusts it in accordance with the measured resistor values. In particular, the circuitry includes a microprocessor 35 for appropriately controlling the circuitry's operating sequence, a multiplexer A 37 for selecting one of the eight resistors, a multiplexer B 39 for selecting either a resistor or the transducer signal for measurement, and an analog-to-digital (A/D) converter 41 for converting the selected measurement to a digital format for compatability with the microprocessor.

The eight resistors R1–R8 are electrically coupled to the multiplexer A 37 over lines 43, and an appropriate digital control signal is coupled to the multiplexer A over a multiplex control bus 45 from the microprocessor 35. The selected resistor is coupled electrically over line 47 to a resistance-to-voltage converter 49, which conducts a current through the resistor to develop a voltage having a magnitude proportional to its resistance. This voltage is coupled over line 51 to a first input terminal of the multiplexer B 39. The microprocessor selects that input terminal by coupling the appropriate digital control signal to the multiplexer B over the multiplex control bus 45. The signal selected by the multiplexer B is coupled over line 53 to the A/D converter 41, which converts the signal to a corresponding digital signal for coupling over an input bus 55 to the microprocessor. The microprocessor sequentially measures each of the eight resistors in this fashion, before it proceeds to monitor the pressure measurement.

As described previously, the phototransistor 27 produces an electrical current indicative of the pressure being measured. Before a measurement of this current is input to the microprocessor 35, however, its value is appropriately adjusted, to partially correct for any inaccuracy in the tranducer's transfer characteristic. The circuitry for performing this partial correction includes a first multiplying digital-to-analog (D/A) converter 57 for adjusting the signal's span, and a second multiplying D/A converter 59 and a summing amplifier 61 for adjusting the signal's zero offset. The electrical current output by the phototransistor is coupled over line 29 to a preamplifier 63 for amplification, and in turn over line 65 to a chopper demodulator 67, whose function is described in detail below. The chopper demodulator outputs an uncorrected pressure measurement signal for coupling over line 69 to the first multiplying D/A converter 57.

The first multiplying D/A converter 57 adjusts the amplitude of the uncorrected pressure measurement signal in accordance with a digital control word supplied by the microprocessor 35 on a span and zero control bus 71. This adjusts the amplitude of the uncorrected signal so that its span for the entire range of possible pressures corresponds to the desired span, i.e., the span for a perfect transducer. The span-corrected signal is coupled on line 73 to a first input terminal of the summing amplifier 61. Connected on line 74 to a second input terminal of the amplifier is a voltage signal corresponding to the transducer's zero offset. This voltage signal is produced by the second multiplying D/A converter 59, which appropriately divides down a reference voltage present at terminal 75, under the control of an appropriate digital word supplied by the microprocessor on the span and zero control bus.

The summing amplifier 61 therefore produces a pressure measurement signal that is corrected for the transducer's zero level error and span error. This partially-corrected measurement signal is coupled over line 77 to the second input terminal of the multiplexer B 39.

After the eight resistors R1-R8 have been measured and the appropriate control words coupled to the first and second multiplying D/A converters 57 and 59, respectively, the microprocessor 35 outputs the appropriate control word to the multiplexer B 39, to select its second input terminal, which carries the partially-corrected pressure measurement signal. This signal is then converted to a corresponding digital signal by the A/D converter 41, and coupled over the input bus 55 to the microprocessor.

The monitoring and correcting circuitry 13 further includes circuitry for stabilizing the intensity of the light emitted by the LED 25. This special circuitry includes a second phototransistor 79 disposed in the transducer connector 15, adjacent to the LED, an associated preamplifier 81, and a differential amplifier 83. The second phototransistor produces a current generally proportional to the light intensity, and this current is coupled over line 85 to the preamplifier, to produce a corresponding voltage signal. The voltage signal is coupled over line 87 to a chopper demodulator 89, whose function is described below, and in turn over line 91 to the negative input terminal of the differential amplifier. The positive input terminal of the amplifier is connected through a resistor divider 93 to the reference voltage appearing at terminal 75. The differential amplifier's output is coupled over line 95 to a chopper modulator 97, whose function is described below, and in turn over line 99 to drive the LED. The resultant feedback loop stabilizes the intensity of the LED's light output at a prescribed level.

The monitoring and correcting circuitry 13 further includes chopper circuitry for preventing any dc offsets in the various circuit elements from affecting the pressure measurement being made. This chopper circuitry includes the previously-mentioned chopper demodulators 67 and 89 and the chopper modulator 97, and in addition includes a 500 Hz signal generator 101. A 500 Hz clock signal produced by the signal generator is coupled over line 103 to each demodulator and to the modulator. The modulator is essentially an analog gate for turning on and off the LED 25 at the 500 Hz rate, so that the electrical current signals produced by the first and second phototransistors 27 and 79, respectively, are modulated correspondingly. The two chopper demodulators, which are essentially sample-and-hold circuits, then function to gate through the corresponding voltage signals only during those times when the LED is energized. As previously mentioned, this chopper circuitry ensures that any dc offsets in the various circuit elements do not affect the accuracy of the pressure measurement being made.

FIG. 4 is a simplified flowchart of the steps performed by the microprocessor 35 in making the successive measurements and corrections described above. In a first step 105, a variable N is set equal to one, and in a following step 107, the microprocessor outputs the appropriate digital words on the multiplex control bus 45 causing the multiplexer A 37 to select input terminal N and the multiplexer B 39 to select input terminal one. In step 109, the microprocessor then reads and stores the digital word appearing on the input bus 55. This word corresponds to the resistance of resistor RN.

In the next step 111 of the program, the microprocessor 35 determines whether or not the variable N is equal to three. If it is, it outputs at step 113 an appropriate correction factor to the second multiplying D/A converter 59, based on its preceding measurements of resistors R1-R3. It then increments the variable N by one at step 115 and returns to the step 107 of selecting input terminals on the two multiplexers 37 and 39. On the other hand, if it is determined at step 111 that N is not equal to three, the program proceeds to step 117 where it is determined whether or not N is equal to six. If it is, the microprocessor at step 119 outputs an appropriate correction factor to the first multiplying D/A converter 57, based on its preceding measurements of resistors R4-R6. It then increments N by one at step 115 and returns to the step 107 of selecting multiplexer input terminals.

If it is determined at step 117 that N is not equal to six, the program proceeds to step 121, where it is determined whether or not N is equal to eight. If it is not equal to eight, the microprocessor increments N by one at step 115, and returns to the step 107 of selecting multiplexer input terminals. If it is determined at step 121 that N is equal to eight, then the microprocessor 35 has completed its measurement of the eight resistors R1-R8, and the program proceeds to step 123, where it calculates a table for linearity correction, based on its preceding measurements of resistors R7 and R8. In step 125, the microprocessor then outputs the appropriate word on the multiplex control bus 45, to select input terminal number two of the multiplexer B 39. In step 127, the microprocessor then reads the digital word present on the input bus 55, which corresponds to the partially-corrected pressure measurement. In step 129, the microprocessor then looks up the appropriate entry in the linearity correction table that was produced in step 123, and adds that entry to the input signal read in step 127, to produce a fully corrected pressure measurement. In step 131, the microprocessor outputs this fully-corrected pressure measurement on lines 133.

The microprocessor 35 outputs a digital word corresponding to the fully-corrected pressure measurement for coupling over lines 133 to both a digital display 135 and a D/A converter 137. The D/A converter, in turn, produces a corresponding analog signal for output by the system on line 18.

It should be appreciated from the foregoing description that the present invention provides an improved transducer system that provides accurate and precise measurements of a physical variable such as pressure for any one of a number of different transducers. Each transducer includes special calibration means for identifying any inaccuracies in its output signal, and monitoring and correcting circuitry is selectively attachable to any one of the transducers, to read the calibration means and appropriately adjust the transducer's output signal, thereby correcting for the identified inaccuracies.

Although the present invention has been described in detail with reference to the presently-preferred embodiment, it should be understood by those of ordinary skill in the art that various modifications can be made without departing from the invention. Accordingly, the invention is limited only by the appending claims.

I claim:

1. A system for selectively measuring one of a plurality of separate physical variables, comprising:
   a plurality of transducer means, each adapted to monitor a separate physical variable and produce a signal indicative thereof, the signal differing from a desired relationship with the physical variable in a predetermined fashion;
   a plurality of characterizing means, each associated with a separate transducer means and characterizing the difference between the signal produced by the transducer means and the desired relationship with the physical variable; and
   a single correcting means, responsive to any selected one of the individual transducer means and its associated characterizing means, for adjusting the transducer means signal in a prescribed fashion, to produce a corrected measurement of the corresponding physical variable.

2. A system as defined in claim 1, wherein:
   each of the plurality of characterizing means characterizes the zero level, span and linearity of the signal produced by its associated transducer means; and
   the correcting means adjusts the signal produced by the selected transducer means by adding to the signal a first correction factor to correct its zero level, multiplying the signal by a second correction factor to correct its span, and adding to the signal a third correction factor to correct its linearity.

3. A system as defined in claim 1, wherein each of the plurality of characterizing means includes a plurality of indicators, a first set of the indicators characterizing the zero level of the difference between the signal produced by the associated transducer means and its desired relationship with the physical variable, a second set of the indicators characterizing the span of the difference between the transducer means signal and its desired relationship with the physical variable, and a third set of the indicators characterizing the linearity of the difference between the transducer means signal and its desired relationship with the physical variable.

4. A system as defined in claim 3, wherein:
   the plurality of indicators of each of the plurality of characterizing means includes a plurality of resistors of prescribed resistance; and
   the correcting means includes means for measuring the resistance of each resistor of the selected characterizing means.

5. A system as defined in claim 1, wherein:
   the system further includes a plurality of carrier means, each carrying a separate transducer means and its corresponding characterizing means; and
   the correcting means includes means for selectively engaging each carrier means and means for reading its characterizing means and adjusting the signal produced by its transducer means, in accordance with the characterizing means.

6. A system as defined in claim 1, wherein each characterizing means characterizes the difference between the signal produced by its corresponding transducer means and the desired relationship with the physical variable for the entire range of possible signal values.

7. A system for selectively measuring one of a plurality of separate physical variables, comprising:
   a plurality of transducer means, each adapted to monitor a separate physical variable and produce a signal indicative thereof, the signal differing from a desired relationship with the physical variable in a predetermined fashion;
   a plurality of characterizing means, each associated with a separate transducer means and characterizing the difference between the signal produced by the transducer means and the desired relationship with the physical variable for the entire range of possible signal values;
   wherein each of the plurality of characterizing means includes a plurality of resistors, a first set of the resistors characterizing the zero level of the difference between the signal produced by the associated transducer means and its desired relationship with the physical variable, a second set of the resistors characterizing the span of the difference between the transducer means signal and its desired relationship with the physical variable, and a third set of the resistors characterizing the linearity of the difference between the transducer means signal and its desired relationship with physical variable;
   a plurality of carrier means, each carrying a separate transducer means and its corresponding characterizing means; and
   a single correcting means including
      means for engaging a selected one of the plurality of carrier means,
      means for measuring the resistance of each resistor of the characterizing means carried by the selected carrier means, and
      means for adjusting the signal produced by the transducer means carried by the selected carrier means by adding to the signal a first correction factor to correct its zero level, multiplying the signal by a second correction factor to correct its span, and adding to the signal a third correction factor to correct its linearity, to produce a corrected measurement of the corresponding physical variable.

8. A disposable transducer apparatus for measuring a prescribed biological parameter and producing a corresponding signal, the apparatus comprising:
   transducer means for measuring a prescribed biological parameter and producing a corresponding signal;
   characterizing means for characterizing the difference between the signal produced by the transducer means and a desired relationship with the biological parameter; and
   compact carrier means for carrying both the transducer means and the characterizing means, wherein the carrier means is adapted for at least partial insertion into a body for measurement of the prescribed biological parameter, wherein the carrier means includes connector means for transmitting the signal produced by the transducer means and for carrying the characterizing means, and wherein the connector means is adapted for selective attachment to an instrument that reads the characterizing means and accordingly adjusts the signal produced by the transducer means.

9. A disposable transducer apparatus as defined in claim 8, wherein the characterizing means characterizes the zero level, span and linearity of the transducer means signal.

10. A disposable transducer apparatus as defined in claim 8, wherein the characterizing means includes at least one resistor, whose resistance characterizes the difference between the transducer means signal and the desired relationship with the prescribed biological parameter.

11. In a system including a plurality of separate transducer means, each for measuring a separate physical variable and producing a corresponding signal, the system further including a single monitoring instrument for monitoring the signal produced by any selected one of the separate transducer means, an improvement comprising:

a plurality of separate characterizing means, each associated with a separate transducer means, for characterizing the difference between the signal produced by the transducer means and a desired relationship with the physical variable; and a plurality of separate carrier means, each carrying a separate transducer means and its associated characterizing means, wherein each carrier means includes connector means for transmitting the signal produced by the transducer means it carries and for carrying the associated characterizing means, and wherein the connector means is adapted for selective attachment to the monitoring instrument, for reading of the characterizing means and adjustment of the transducer means signal, accordingly.

12. An improvement as defined in claim 11, wherein the characterizing means characterizes the zero level, span and linearity of the transducer means signal.

13. An improvement as defined in claim 11, wherein the characterizing means includes at least one resistor, whose resistance characterizes the difference between the transducer means signal and the desired relationship with the prescribed physical variable.

14. A method for measuring any selected one of a plurality of separate physical variables, comprising steps of:

selecting a particular one of a plurality of transducer means, each adapted to monitor a separate physical variable and produce a corresponding signal, and each having a separate, associated characterizing means for characterizing the difference between the transducer means signal and a desired relationship with the physical variable;

measuring the output signal produced by the selected transducer means;

reading the characterizing means associated with the selected transducer means, to determine the difference between the transducer means signal and its desired relationship with the physical variable; and adjusting the particular transducer means signal using a single means responsive to any of the transducer means and associated characterizing means but responding in accordance with the particular difference determined in the step of reading, to produce a corrected measure of the physical variable.

15. A method as defined in claim 14, wherein:

the characterizing means associated with the selected transducer means characterizes the zero level, span and linearity of the transducer means signal; and the step of adjusting includes steps of adding to the signal a first correction factor to correct its zero level, multiplying the signal by a second correction factor to correct its span, and adding to the signal a third correction factor to correct its linearity.

16. A method as defined in claim 14, wherein:

the characterizing means associated with the selected transducer means includes a plurality of resistors having prescribed resistances that characterize the difference between the transducer means signal and the desired relationship with the physical variable; and the step of reading includes a step of measuring the resistance of each resistor.

17. A method as defined in claim 14, wherein:

the characterizing means associated with the selected transducer means includes a plurality of indicators; and the step of adjusting includes steps of adjusting the zero level of the transducer means signal in accordance with a first set of the indicators, adjusting the span of the transducer means signal in accordance with a second set of the indicators, and adjusting the linearity of the transducer means signal in accordance with a third set of the indicators.

* * * * *

REEXAMINATION CERTIFICATE (1557th)
United States Patent [19]
Bailey

[11] B1 4,446,715
[45] Certificate Issued Sep. 17, 1991

[54] TRANSDUCER CALIBRATION SYSTEM

[75] Inventor: Wilber H. Bailey, Leucadia, Calif.

[73] Assignee: Camino Laboratories, Inc.

Reexamination Request:
No. 90/002,106, Aug. 9, 1990

Reexamination Certificate for:
Patent No.: 4,446,715
Issued: May 8, 1984
Appl. No.: 385,492
Filed: Jun. 7, 1982

[51] Int. Cl.[5] .................. G01D 21/00; G01K 15/00; G01L 27/00
[52] U.S. Cl. .................. 73/1 R; 128/634; 128/667; 128/675; 128/736; 128/748; 364/571.02; 364/571.04; 364/571.06; 374/1; 374/143
[58] Field of Search ............ 73/1 R, 866.1, 4 R, 73/4 V, 4 D; 324/130; 364/571.01–571.08, 573; 374/1, 2, 143; 128/634, 667, 675, 736, 748

[56] References Cited
U.S. PATENT DOCUMENTS

| | | | |
|---|---|---|---|
| 2,951,200 | 8/1960 | Critchlow | 364/571.01 X |
| 3,439,258 | 4/1969 | Van Leeuwen | 323/367 |
| 3,531,978 | 10/1970 | Yeager | 73/4 V |
| 3,535,637 | 10/1970 | Goransson | 324/130 |
| 3,740,533 | 6/1973 | Van Zeggeler | 73/1 R X |
| 3,757,217 | 9/1973 | Pearson | 324/151 R |
| 3,790,910 | 2/1974 | McCormack | 75/4 R X |
| 3,905,229 | 9/1975 | Togo et al. | 364/571.03 X |
| 3,976,150 | 8/1976 | Wilson et al. | 73/866.1 X |
| 4,000,643 | 1/1977 | Pearson | 364/571.01 |
| 4,038,532 | 7/1977 | Burris et al. | 364/571.08 X |
| 4,064,396 | 12/1977 | Panarello | 364/573 |
| 4,082,998 | 4/1978 | Marriott | 324/130 X |
| 4,179,745 | 12/1979 | Wuertele | 364/571.05 |
| 4,192,005 | 3/1980 | Kurtz | 364/571.03 |
| 4,218,916 | 8/1980 | Mutziger | 73/866.1 X |
| 4,263,803 | 4/1981 | Burkhardt | 74/1 R |
| 4,282,578 | 8/1981 | Payne et al. | 364/573 |
| 4,286,868 | 9/1981 | Leska | 355/77 X |
| 4,290,297 | 9/1981 | Anderson | 73/1 R |
| 4,303,984 | 12/1981 | Houvig | 364/571.07 |
| 4,323,972 | 4/1982 | Winter | 364/571.05 X |
| 4,331,026 | 5/1982 | Howard et al. | 73/1 R X |
| 4,337,638 | 7/1982 | Leonard et al. | 73/1 H |
| 4,349,886 | 9/1982 | Ibar | 364/571.02 X |
| 4,399,515 | 8/1983 | Cross | 364/571.03 |
| 4,418,392 | 11/1983 | Hata | 364/571.07 |
| 4,437,164 | 3/1984 | Branch, III | 364/571.03 |
| 4,462,082 | 7/1984 | Thiele et al. | 364/571.04 |
| 4,473,797 | 9/1984 | Shiota | 364/571.04 X |

OTHER PUBLICATIONS

"Nth Order Regression", Science and Engineering Programs Apple II Edition, 1981, pp. 16–18.

*Primary Examiner*—Thomas P. Noland

[57] ABSTRACT

A transducer system that provides accurate measurements of a physical variable such as pressure for any one of a number of different transducers. Each transducer includes special calibration indicators for identifying any inaccuracies, in its output signal, and monitoring and correcting circuitry is selectively attachable to any one of the transducers, to read the calibration indicators and appropriately adjust the transducer's output signal, thereby correcting for the identified inaccuracies.

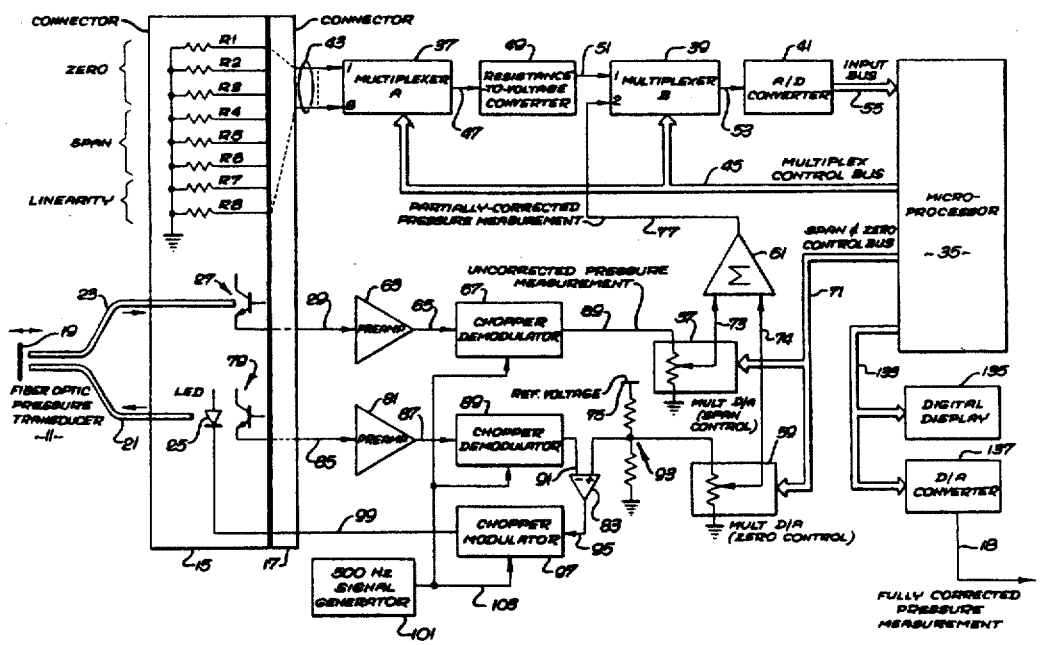

B1 4,446,715

REEXAMINATION CERTIFICATE ISSUED UNDER 35 U.S.C. 307

THE PATENT IS HEREBY AMENDED AS INDICATED BELOW.

Matter enclosed in heavy brackets [] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claim 7 is confirmed.

Claims 1-3, 5, 6, 8-12 and 14-17 are determined to be patentable as amended.

Claims 4 and 13 dependent on an amended claim, are determined to be patentable.

New claims 18-56 are added and determined to be patentable.

1. A system for selectively measuring one of a plurality of separate physical variables, comprising:
   a plurality of transducer means, each adapted to monitor a separate physical variable and produce a signal indicative thereof, the signal differing from a desired relationship with the physical variable in a predetermined fashion;
   a plurality of *passive* characterizing means, each associated with a separate transducer means and *each* characterizing *with at least one passive indicator* the difference between the signal produced by [the] *its respective* transducer means and the desired relationship with the physical variable; and
   a single correcting means, responsive to any selected one of the individual transducer means and its associated characterizing means, for adjusting the transducer means signal in a prescribed fashion, to produce a corrected measurement of the corresponding physical variable.

2. A system as defined in claim 1, wherein:
   each of the plurality of *passive* characterizing means characterizes the zero level, span and linearity of the signal produced by its associated transducer means; and
   the correcting means adjusts the signal produced by the selected transducer means by adding to the signal a first correction factor to correct its zero level, multiplying the signal by a second correction factor to correct its span, and adding to the signal a third correction factor to correct its linearity.

3. A system as defined in claim 1, wherein each of the plurality of *passive* characterizing means includes a plurality of *passive* indicators, a first set of the *passive* indicators characterizing the zero level of the difference between the signal produced by the associated transducer means and its desired relationship with the physical variable, a second set of the *passive* indicators characterizing the span of the difference between the transducer means signal and its desired relationship with the physical variable, and a third set of the *passive* indicators characterizing the linearity of the difference between the transducer means signal and its desired relationship with the physical variable.

5. A system as defined in claim 1, wherein:
   the system further includes a plurality of carrier means, each carrying a separate transducer means and its corresponding *passive* characterizing means; and
   the correcting means includes means for selectively engaging each carrier means and means for reading its *passive* characterizing means and adjusting the signal produced by its transducer means, in accordance with the characterizing means.

6. A system as defined in claim 1, wherein each *passive* characterizing means characterizes the difference between the signal produced by its corresponding transducer means and the desired relationship with the physical variable for the entire range of possible signal values.

8. A disposable transducer apparatus for measuring a prescribed biological parameter and producing a corresponding signal, the apparatus comprising:
   transducer means for measuring [a] *the* prescribed biological parameter and producing a corresponding signal *differing from the biological parameter in a known manner*;
   passive characterizing means for characterizing *with at least one passive indicator* the difference between the signal produced by the transducer means and a desired relationship with the biological parameter; and
   compact carrier means for carrying both the transducer means and the *passive* characterizing means, wherein the carrier means is adapted for at least partial insertion into a body for measurement of the prescribed biological parameter, wherein the carrier means includes connector means for transmitting the signal produced by the transducer means and for carrying the *passive* characterizing means, and wherein the connector means is adapted for selective attachment to an instrument that reads the *passive* characterizing means and accordingly adjusts the signal produced by the transducer means.

9. A disposable transducer apparatus as defined in claim 8, wherein the *passive* characterizing means characterizes the zero level, span and linearity of the transducer means signal.

10. A disposable transducer apparatus as defined in claim 8, wherein the *passive* characterizing means includes at least one resistor, whose resistance characterizes the difference between the transducer means signal and the desired relationship with the prescribed biological parameter.

11. In a system including a plurality of separate transducer means, each for measuring a separate physical variable and producing a corresponding signal, the system further including a single monitoring instrument for monitoring the signal produced by any selected one of the separate transducer means, an improvement comprising:
   a plurality of separate *passive* characterizing means, each associated with a separate transducer means, *and each* for characterizing *with at least one passive indicator* the difference between the signal produced by [the] *its respective* [the] transducer means and a desired relationship with the physical variable; and
   a plurality of separate carrier means, each carrying a separate transducer means and its associated characterizing means, wherein each carrier means includes connector means for transmitting the signal produced by the transducer means it carries and for carrying the associated *passive* characterizing means, and wherein the connector means is adapted for selective attachment to the monitoring instrument, for reading of the *passive* characterizing means and adjustment of the transducer means signal, accordingly.

12. An improvement as defined in claim 11, wherein the *passive* characterizing means characterizes the zero level, span and linearity of the transducer means signal.

14. A method for measuring any selected one of a plurality of separate physical variables, comprising steps of:

selecting a particular one of a plurality of transducer means, each adapted to monitor a separate physical variable and produce a corresponding signal, *the signal differing from a desired relationship with the physical variable in a known manner,* and each having a separate, associated *passive* characterizing means for characterizing *with at least one passive indicator* the difference between the *respective* transducer means signal and [a] the desired relationship with the physical variable;

measuring the output signal produced by the selected transducer means;

reading the *passive* characterizing means associated with the selected transducer means, to determine the difference between the transducer means signal and its desired relationship with the physical variable; and adjusting the particular transducer means signal using a single means responsive to any of the transducer means and associated *passive* characterizing means but responding in accordance with the particular difference determined in the step of reading, to produce a corrected measure of the physical variable.

15. A method as defined in claim 14, wherein:

the *passive* characterizing means associated with the selected transducer means characterizes the zero level, span and linearity of the transducer means signal; and the step of adjusting includes steps of adding to the signal a first correction factor to correct its zero level, multiplying the signal by a second correction factor to correct its span, and adding to the signal a third correction factor to correct its linearity.

16. A method as defined in claim 14 wherein:

the *passive* characterizing means associated with the selected transducer means includes a plurality of resistors having prescribed resistances that characterize the difference between the transducer means signal and the desired relationship with the physical variable; and the step of reading includes a step of measuring the resistance of each resistor.

17. A method as defined in claim 14, wherein: the *passive* characterizing means associated with the selected transducer means includes a plurality of *passive* indicators; and the step of adjusting includes steps of adjusting the zero level of the transducer means signal in accordance with a first set of the indicators, adjusting the span of the transducer means signal in accordance with a second set of the indicators, - and adjusting the linearity of the transducer means signal in accordance with a third set of the indicators.

18. A system for selectively measuring one of a plurality of separate physical variables, comprising:

a plurality of transducer means, each adapted to monitor a separate physical variable and produce a signal indicative thereof, the signal differing from a desired relationship with the physical variable in a predetermined fashion:

a plurality of characterizing means, each associated with a separate transducer means and characterizing the difference between the signal produced by the transducer means and the desired relationship with the physical variable;

wherein each of the plurality of characterizing means includes a plurality of indicators, a first set of the indicators characterizing the zero level of the difference between the signal produce by the associated transducer means and its desired relationship with the physical variable, a second set of the indicators characterizing the span of the difference between the transducer means signal and its desired relationship with the physical variable, and a third set of the indicators characterizing the linearity of the difference between the transducer means signal and its desired relationship with the physical variable;

wherein the plurality of indicators of each of the plurality of characterizing means includes a plurality of resistors of prescribed resistance;

a single correcting means, responsive to any selected one of the individual transducer means and its associated characterizing means, for adjusting the transducer means signal in a prescribed fashion, to produce a corrected measurement of the corresponding physical variable;

wherein the correcting means includes means for measuring the resistance of each resistor of the selected characterizing means.

19. A disposable transducer apparatus for measuring a prescribed biological parameter and producing a corresponding signal, the apparatus comprising:

transducer means for measuring a prescribed biological parameter and producing a corresponding signal;

characterizing means for characterizing the difference between the signal produced by the transducer means and a desired relationship with the biological parameter wherein the characterizing means includes at least one resistor, whose resistance characterizes the difference between the transducer means signal and the desired relationship with the prescribed biological parameter; and compact carrier means for carrying both the transducer means and the characterizing means, wherein the carrier means is adapted for at least partial insertion into a body for measurement of the prescribed biological parameter, wherein the carrier means includes connector means for transmitting the signal produced by the transducer means and for carrying the characterizing means, and wherein the connector means is adapted for selective attachment to an instrument that reads the characterizing means and accordingly adjusts the signal produced by the transducer means.

20. In a system including a plurality of separate transducer means, each for measuring a separate physical variable and producing a corresponding signal, the system further including a single monitoring instrument for monitoring the signal produced by any selected one of the separate transducer means, an improvement comprising:

a plurality of separate characterizing means, each associated with a separate transducer means, for characterizing the difference between the signal produced by the transducer means and a desired relationship with the physical variable wherein each characterizing means includes at least one resistor, whose resistance characterizes the difference between the transducer means signal and the desired relationship with the prescribed physical variable;

a plurality of separate carrier means, each carrying a separate transducer means and its associated characterizing means, wherein each carrier means includes connector means for transmitting the signal produced by the transducer means it carries and for carrying the associated characterizing means, and wherein the connector means is adapted for selective attachment to the monitoring instrument, for reading of the characterizing means and adjustment of the transducer means signal, accordingly.

21. A method for measuring any selected one of a plurality of separate physical variables, comprising the steps of:

selecting a particular one of a plurality of transducer means, each adapted to monitor a separate physical variable and produce a corresponding signal, and each having a separate, associated characterizing means for characterizing the difference between the transducer means signal and a desired relationship with the physical variable wherein the characterizing means associated with the selected transducer means includes a plurality of resistors having prescribed resistances that characterize the difference between the transducer means signal and the desired relationship with the physical variable;

measuring the output signal produced by the selected transducer means;

reading the characterizing means associated with the selected transducer means, to determine the difference between the transducer means signal and its desired relationship with the physical variable including measuring the resistance of each resistor; and adjusting the particular transducer means signal using a single means responsive to any of the transducer means and associated characterizing means but responding in accordance with the particular difference determined in the step of reading, to produce a corrected measure of the physical varible.

22. The system of claim 1 wherein each passive characterizing means characterizes the zero level, span and linearity of the difference between its respective transducer signal and the desired relationship.

23. The system of claim 1 wherein:

each passive characterizing means comprises an array of passive indicators, a physical characteristic of each indicator being selected to indicate a characterization value of said difference; and the single correcting means is responsive to the characterization values for adjusting the signal from the transducer means.

24. The system of claim 23 wherein the indicators comprise resistors having resistance values selected to indicate the characterization values.

25. The system of claim 1 wherein:

the single correcting means applies at least one characterization to the transducer signal when the transducer signal is in an analog form to result in a partially corrected signal;

the system further comprises digital conversion means for converting the partially corrected signal to a digital form; and the single correcting means applies at least one characterization to the digitized, partially corrected signal to produce the corrected measurement.

26. The system of claim 25 wherein:

the single correcting means applies to the zero level and the span characterization to the transducer means signal when said signal is in an analog form to provide the partially corrected signal; and the correcting means applies the linearity characterization to the digitized, partially corrected signal to result in the corrected measurement.

27. The system of claim 1 wherein:

each of the plurality of passive characterizing means characterizes the difference between a continuous curve which generally represents the uncorrected signal produced by its respective transducer means and a continuous curve which generally represents the desired relationship with the physical variable, and each provides curve correction coefficients which represent the difference between the shapes of the two representative curves; and the single correcting means is responsive to the curve correction coefficients from the passive characterization means for applying the correction coefficients to the signal from the respective transducer means to produce the corrected mesurement.

28. The system of claim 1, wherein the single correcting means comprises:

reading means for applying a uniform energy source to the passive characterizing means such that each passive characterizing means provides a characterization signal characterizing the difference between the signal produced by its respective transducer means and the desired relationship with the physical variable; and adjusting means responsive to the characterization signal for adjusting the respective transducer means signal in a prescribed fashion to produce a corrected measurement of the corresponding variable.

29. The apparatus of claim 8 wherein:

the passive characterizing means comprises an array of passive indicators, a physical characteristic of each indicator being selected to indicate a characterization value; and the instrument is responsive to the characterization values for adjusting the transducer means signal accordingly.

30. The system of claim 29 wherein the indicators comprise resistors having resistance values selected to indicate the characterization values.

31. The apparatus of claim 8 wherein:

the single correcting means applies at least one characterization to the transducer signal when the transducer signal is in an analog form to result in a partially corrected signal;

the system further comprises digital conversion means for converting the partially corrected signal to a digital form; and the correcting means applies at least one characterization to the digitized, partially corrected signal to produce the corrected measurement.

32. The apparatus of claim 31 wherein:

the instrument applies the zero level and the span correction coefficients to the transducer means signal when

*said signal is in an analog form to provide the partially corrected signal; and*

*the instrument applies the linearity correction coefficient to the digitized, partially corrected signal.*

33. The apparatus of claim 8 wherein:

the passive characterizing means characterizes the difference between a continuous curve generally representative of the unadjusted signal produced by the transducer means and a continuous curve generally representative of the biological parameter and provides curve correction coefficients which represent the difference between the shapes of the two representative curves; and the instrument is responsive to the correction coefficients from the passive characterization means for applying the curve correction coefficients to the signal from the transducer means to produce the adjusted signal.

34. The apparatus of claim 8 wherein the instrument comprises:

reading means for applying a uniform energy source to the passive characterizing means such that the passive characterizing means provides a characterization signal characterizing the difference between the signal produced by the transducer means and the desired relationship with the biological parameter; and adjusting means responsive to the characterization signal for adjusting the transducer means signal in a prescribed fashion to produce a corrected measurement of the corresponding biological parameter.

35. The improvement of claim 11 wherein:

each passive characterizing means comprises an array of passive indicators, a physical characteristic of each indicator being selected to indicate a characterization value; and the single monitoring instrument is adapted to read the array of passive indicators and adjust the signal produced by the respective transducer means in response thereto.

36. The improvement of claim 35 wherein the indicators comprise resistors having resistance values selected to indicate the characterization values.

37. The improvement of claim 11 wherein:

the single monitoring instrument applies at least one characterization to the transducer means signal when the transducer means signal is in an analog form to result in a partially corrected signal;

the system further comprises digital conversion means for converting the partially corrected signal to a digital form; and the single monitoring instrument applies at least one-characterization to the digitized, partially corrected signal to produce the adjusted signal.

38. The improvement of claim 37 wherein the single monitoring instrument applies the zero level and the span correction coefficients to the transducer means signal when said signal is in an analog form to provide the partially corrected signal; and the single monitoring instrument applies the linearity correction coefficient to the digitized, partially corrected signal to result in the corrected measurement.

39. The improvement of claim 11 wherein:

each of the plurality of passive characterizing means characterizes the difference between a continuous curve generally representative of the unadjusted signal produced by its respective transducer means and a continuous curve generally representative of the physical variable and each for providing correction coefficients which represent the difference between the shapes of the two representative curves; and the monitoring instrument responsive to the curve correction coefficients from the respective passive characterization means for applying the correction coefficients to the signal from the transducer means to adjust said signal.

40. The improvement of claim 11 wherein the single monitoring instrument comprises:

reading means for applying a uniform energy source to the passive characterizing means such that the passive characterizing means provides a characterization signal characterizing the difference between the signal produced by the selected transducer means and the physical variable; and adjusting means responsive to the characterization signal for adjusting the transducer means signal in a prescribed fashion, to produce a corrected measurement of the corresponding variable.

41. The method of claim 14 wherein the step of selecting comprises the step of characterizing with each passive characterizing means the zero level, span and linearity of the difference between its respective transducer signal and the desired relationship.

42. The method of claim 14 wherein:

the step of selecting comprises the steps of forming each passive characterizing means of an array of passive indicators, and selecting a physical characteristic of each indicator to indicate a characterization value;

the step of reading comprises reading the array of passive indicators; and the step of adjusting comprises adjusting the transducer means signal responsive to the characterization values read from the array.

43. The method of claim 42 wherein the step of forming comprises the steps of providing resistors as indicators and selecting the resistance values of said resistors to indicate the characterization values.

44. The method of claim 14 wherein the step of adjusting comprises the steps of:

applying at least one characterization to the transducer signal when the transducer signal is in an analog form to result in a partially corrected signal;

converting the partially corrected signal to a digital form; and applying at least one characterization to the digitized partially corrected signal to produce the corrected measurement.

45. The method of claim 44 wherein:

the step of applying at least one characterization when the transducer signal is in an analog form comprises applying the zero level and the span correction coefficients to the transducer means signal to provide the partially corrected signal; and the step of applying at least one characterization to the digitized, partially corrected signal comprises the step of applying the linearity correction coefficient to result in the corrected measurement.

46. The method of claim 14 further comprising the steps of:

characterizing the difference between a continuous curve generally representative of the uncorrected signal produced by a transducer means and a continuous curve generally representative of the desired relationship with the physical variable, and providing curve correction coefficients which represent the difference between the shapes of the two representative curves; and the step of adjusting comprises receiving the curve correction coefficients from the respective passive characterization means and applying the correction coefficients to the transducer means signal to produce the corrected measurement.

47. The method of claim 14 wherein the step of adjusting comprises the steps of:
applying a uniform energy source to the selected passive characterizing means such that the passive characterizing means produces a characterization signal characterizing the difference between the signal produced by the transducer means and the desired relationship with the physical variable; and
adjusting the transducer means signal in a prescribed fashion in response to the characterization signal to produce a corrected measurement of the corresponding variable.

48. A system for selectively measuring one of a plurality of physical variables, comprising:
a plurality of transducers, each adapted to monitor a physical variable and produce an uncorrected signal indicative thereof, the signal differing from a desired relationship with the physical variable in a known manner;
a plurality of passive characterizing means, each associated with a separate transducer and each for characterizing with at least one passive indicator the difference between a continuous curve generally representative of the uncorrected signal produced by its respective transducer and a continuous curve generally representative of the desired relationship with the physical variable, and each for providing curve correction coefficients which represent the difference between the shapes of the two representative curves; and
a single correcting means, responsive to any selected one of the individual transducers for receiving the uncorrected signal from the transducer, and responsive to the curve correction coefficients from the respective passive characterization means for applying the correction coefficients to the uncorrected signal from the transducer to produce a corrected measurement of the corresponding physical variable.

49. The system of claim 48 wherein each passive characterizing means characterizes the zero level, span and linearity of the difference between its respective transducer signal and the desired relationship.

50. The system of claim 48 wherein each passive characterizing means comprises an array of passive indicators, a physical characteristic of each indicator being selected to indicate a characterization value of said difference; and
the single correcting means is responsive to the characterization values to produce the corrected measurement.

51. The system of claim 50 wherein the indicators comprise resistors having resistance values selected to indicate the characterization values.

52. The system of claim 48 wherein:
the single correcting means applies at least one characterization to the transducer signal when the transducer signal is in an analog form to result in a partially corrected signal;
the system further comprises digital conversion means for converting the partially corrected signal to a digital form; and
the correcting means applies at least one characterization to the digitized, partially corrected signal to produce the corrected measurement.

53. The system of claim 52 wherein:
the single correcting means applies the zero level and the span correction coefficients to the uncorrected signal when the uncorrected signal is in an analog form to provide the partially corrected signal; and
the single correcting means further applies the linearity correction coefficient to the digitized, partially corrected signal to result in the corrected measurement.

54. The system of claim 48 wherein the single correcting means comprises:
reading means for applying a uniform energy source to the passive characterizing means such that the passive characterizing means provides a characterization signal characterizing the difference between the signal produced by the selected transducer means and the desired relationship with the physical variable; and
adjusting means responsive to the characterization signal for adjusting the transducer means signal in a prescribed fashion to produce a corrected measurement of the corresponding variable.

55. The system of claim 48 wherein the curve correction coefficients comprise zero level, span and linearity correction coefficients and the correcting means applies said correction coefficients to the uncorrected signal in accordance with the following:

$$P = A_0 + A_1 x + A_2 x^2$$

where:
P = corrected measurement
$A_0$ = zero level correction coefficient
$A_1$ = span correction coefficient
$A_2$ = linearity correction coefficient
x = uncorrected signal.

56. The system of claim 48 further comprising a carrier means for providing a disposable carrier unit containing both the transducer and its associated characterizing means which may be removably connected to the single correcting means.

* * * * *